United States Patent [19]

Rosenblum

[11] 3,968,696

[45] July 13, 1976

[54] DEVICE FOR TAKING SAMPLES OF SLURRIES OR OF ANY SUSPENSION OF PARTICULATE MATERIAL IN LIQUID AND FOR MEASURING DESIRED CHEMICAL OR PHYSICAL PROPERTIES OF SUCH SAMPLES

[75] Inventor: Frank Rosenblum, Ville St. Laurent, Canada

[73] Assignee: Noranda Mines Limited, Ontario, Canada

[22] Filed: Mar. 6, 1975

[21] Appl. No.: 555,719

[30] Foreign Application Priority Data
Apr. 3, 1974 Canada .............................. 196721

[52] U.S. Cl. ............................... 73/425.4 R; 73/354
[51] Int. Cl.² ........................................... G01N 1/12
[58] Field of Search ......... 73/425.2, 425.4 R, 425.6, 73/354

[56] References Cited
UNITED STATES PATENTS 1,761,298  6/1930  Harris ............................... 73/425.4
2,342,441  2/1944  Will ..................................... 73/354
3,349,624  10/1967  Fraga ............................. 73/425.4 R
3,531,995  10/1970  Barker .......................... 73/425.4 R

*Primary Examiner*—S. Clement Swisher
*Attorney, Agent, or Firm*—Fleit & Jacobson

[57] ABSTRACT

A novel device is disclosed for taking samples of slurries of ground ore or minerals in water, or any suspension of particulate materials in liquid with no restriction on the particulate material content of the sample. The device comprises a container provided with movable end closures, such container being attached to a holder of suitable length to enable it to be immersed to the required depth into a body of slurry or liquid. Means are associated with the holder for tightly closing the end closures and for opening at least one of such end closures. The device may further be provided with an apparatus for measuring in situ desired chemical or physical properties of such sample.

20 Claims, 11 Drawing Figures

DEVICE FOR TAKING SAMPLES OF SLURRIES OR OF ANY SUSPENSION OF PARTICULATE MATERIAL IN LIQUID AND FOR MEASURING DESIRED CHEMICAL OR PHYSICAL PROPERTIES OF SUCH SAMPLES

The invention relates to a novel device for taking samples of slurries of ground ore or minerals in water, or, more generally, any suspension of particulate material in liquid, with no restriction on the particulate material content of the sample.

It is the object of the present invention to provide a sampler which, contrary to most of the conventional samplers, will permit to collect a representative sample from any specific location within a body of slurry or liquid, and to withdraw such sample without further contact with it. Such sampler is sealed during immersion so that the inside thereof remains uncontaminated prior to taking the samples. It is also sealed after taking the sample so that the sample is withdrawn without further contact with the body of slurry or liquid from which it is taken.

The sampler, in accordance with the invention, comprises a container provided with side walls which are closed by movable end closures. The container is attached to a holder of suitable length to enable it to be immersed to the required depth into the body of slurry or liquid. Means are associated with the holder for tightly closing the end closures and for opening at least one of such end closures.

The means for closing and opening the end closures comprises separate connections associated with the holder and attached to the end closures, a handle assembly mounted at the other end of the holder and including separate handles for operating such connections, and spring means also mounted on the holder for biasing the connections with respect to each other in a direction such as to tightly close the end closures.

In a preferred embodiment of the invention, the holder is a straight tube and the connections include a first tube free to move longitudinally inside the holder and attached at one end to one of the end closures, and a second tube free to move longitudinally outside the holder and attached at one end to the other end closure. One of the tubes is secured to its associated end closure by a flexible joint so as to further ensure tight sealing of the closures against the container. The operating handles are fixed to the other end of the tubes and the handle assembly further comprises an additional handle fixed to the other end of the holder. Separate springs are mounted coaxially with the tubes and placed between the operating handles and such additional handle for biasing the operating handles away from the additonal handle and so close the end closures.

The holder may be secured to the container by means of a spider member having its arms attached to the walls of the container and its hub secured to the holder. The walls of the container may take various forms but, in a preferred embodiment of the invention, the container has a cylindrical wall and the spider member is secured to a ring of nearly the same diameter as the cylindrical wall. The cylindrical wall is threaded onto such ring so as to permit the attachment of cylindrical walls of various lengths to suit any volume of sample.

The sampler, in accordance with the invention, may further comprise means associated with one of the end closures for measuring in situ desired chemical or physical properties of the samples. Such means include a sealed housing enclosing a motor having a shaft protruding through such one end closure for operating a stirrer located in such container, and suitable apparatus also protruding through such one end closure and adapted to contact the sample contained in the container for measuring the desired properties thereof.

In a preferred embodiment of the invention, the holder is a straight tube which is secured to the container through a first spider member having its hub secured to the straight tube and its arms secured to the walls of the container through rods extending from such arms to the walls. The connections for closing and opening the container include a first tube free to move longitudinally inside the holder and attached to one end of the housing, and a second tube free to move longitudinally outside the holder and which is secured to the other end closure through a second spider member having its hub secured to the second tube and its arms secured to the other end closure through rods extending from such arms to the other end closure. The housing and container are provided with outer flanges or rings through which the rods extending from the first and second spider members pass so as to ensure perfect alignment of the container and of the other end closure. The springs for biasing the end closures in closed position are mounted coaxially with the tubes and placed between the first and second spider members and between the housing and the first spider member respectively so as to hermetically close the container. The second spider member is secured to the other end closure through a flexible joint so as to further ensure perfect sealing of the container.

The handle assembly of the above mentioned preferred embodiment of the invention may comprise a reference handle secured to the other end of the holder and the operating handles pivotally mounted on such reference handle. Means may be provided for locking the operating handles in operated position for maintaining the container open if desired while it is immersed in the body of slurry or liquid. The handle assembly may further comprise a control handle mounted on the other end of the second tube and such control handle provided with a manual switch for energizing the motor operating the stirrer. A control box may also be mounted on the other end of the first tube for controlling the motor and the various apparatus located in the housing.

The invention will now be disclosed, by way of example, with reference to preferred embodiments thereof illustrated in the accompanying drawings wherein.

Figure 1:
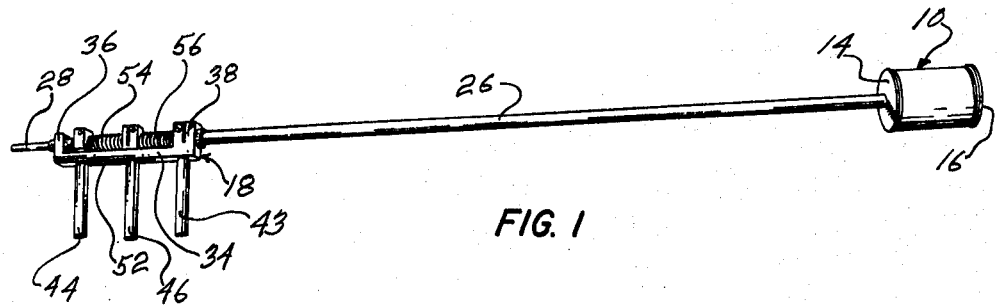
FIGS. 1 and 2 illustrate perspective views of an embodiment of a sampler device in accordance with the invention, shown in the closed and open positions respectively.
Figure 2:
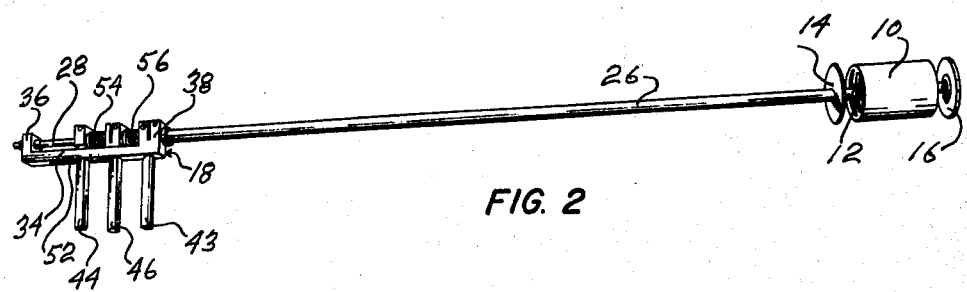

Referring to FIGS. 1 and 2 of the drawings, there is shown generally a sampler device comprising a container 10 secured to a holder 12 of suitable length for immersing the container into a body of slurry or liquid and provided with end closures 14 and 16 operated by suitable means connected to a handle assembly 18.

Figure 4:
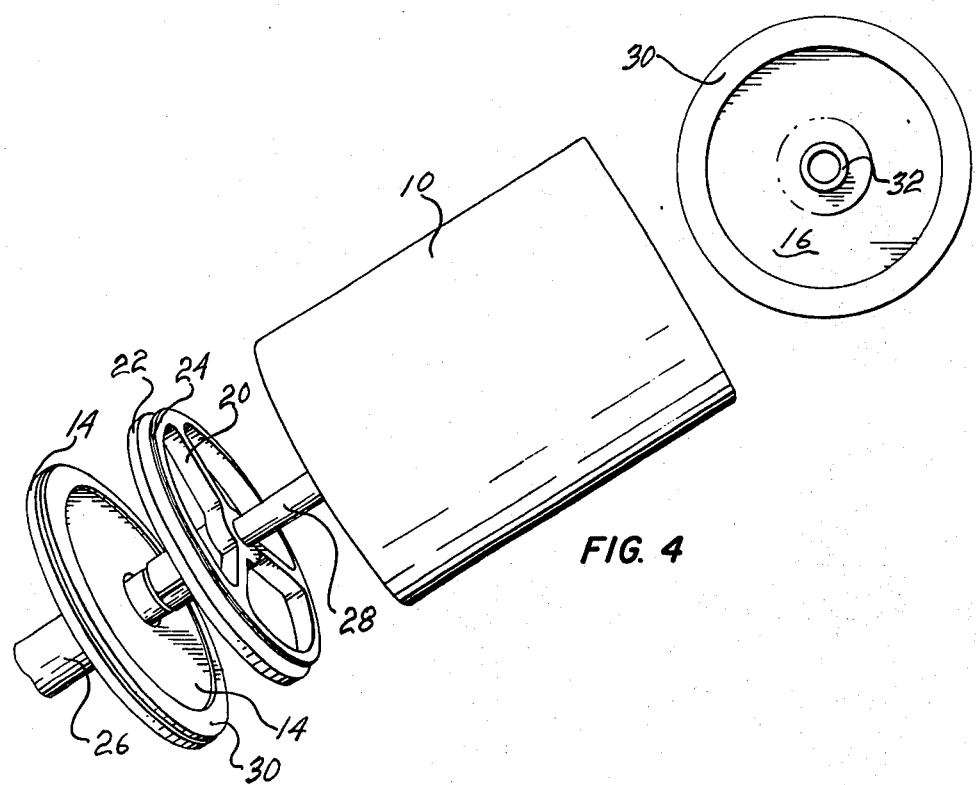
FIG. 4 illustrates an exploded view of the container of the sampler device of FIG. 3.
Figure 3:
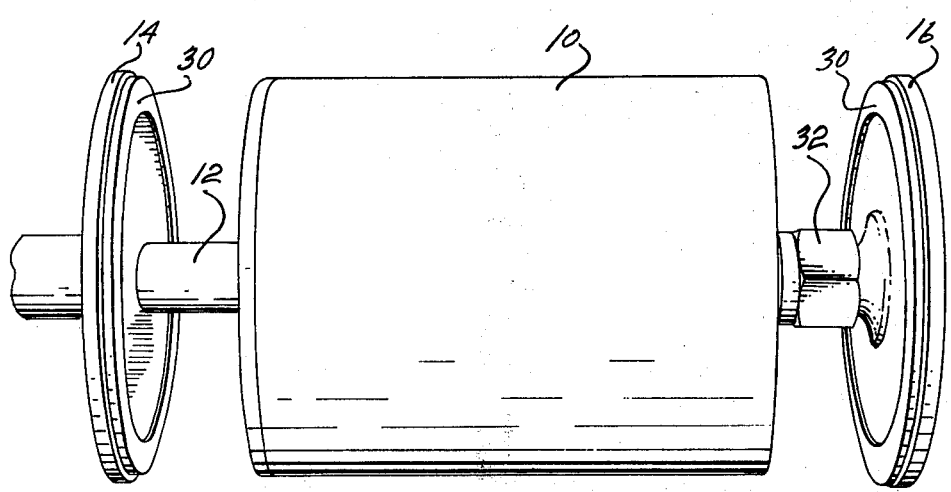
FIG. 3 illustrates an enlarged view of the container of the sampler device of FIGS. 1 and 2 shown in the open position.

Referring more particularly to FIGS. 3 and 4, holder 12 is secured to the hub of a spider member 20 the arms of which are connected to a ring 22. The container 10 is a cylinder which is secured to the ring 22 through a threaded connection 24 which permits to easily replace a cylinder of a given length by a shorter or longer cylinder so as to suit various volumes of liquid. It is to be understood that the container 10 does not necessarily have to be a cylinder and that the walls of the container may take various forms. In addition, other means of securing the holder 12 to the container 10 are also envisaged.

In the embodiment illustrated in FIGS. 1 to 5 of the drawings, the holder 12 is a straight tube and the connections for operating the end closures 14 and 16 consist of tubes 26 and 28 which are concentric with holder 12 and free to move longitudinally outside and inside the holder respectively. It is to be understood that the holder 12 need not be straight but could incorporate a change in direction. In such a case, flexible means may be easily provided to operate the end closures. In any case, it is to be understood that the means disclosed for operating end closures 14 and 16 are only by way of example and that other arrangements are also envisaged.

As illustrated more particularly in FIGS. 3 and 4, tube 26 is secured to end closure 14 whereas tube 28 is secured to end closure 16. Gaskets 30 are provided at the periphery of the end closures to perfectly seal the container when closed. In addition, tube 26 is secured to end closure 16 through a flexible ball joint 23 which further ensures tight sealing of the end closures against the container wall. In the present embodiment, the gasket 30 of end closure 14 is adapted to contact ring 22 but in other types of containers, it could close directly on the wall of the container.

Figure 5:
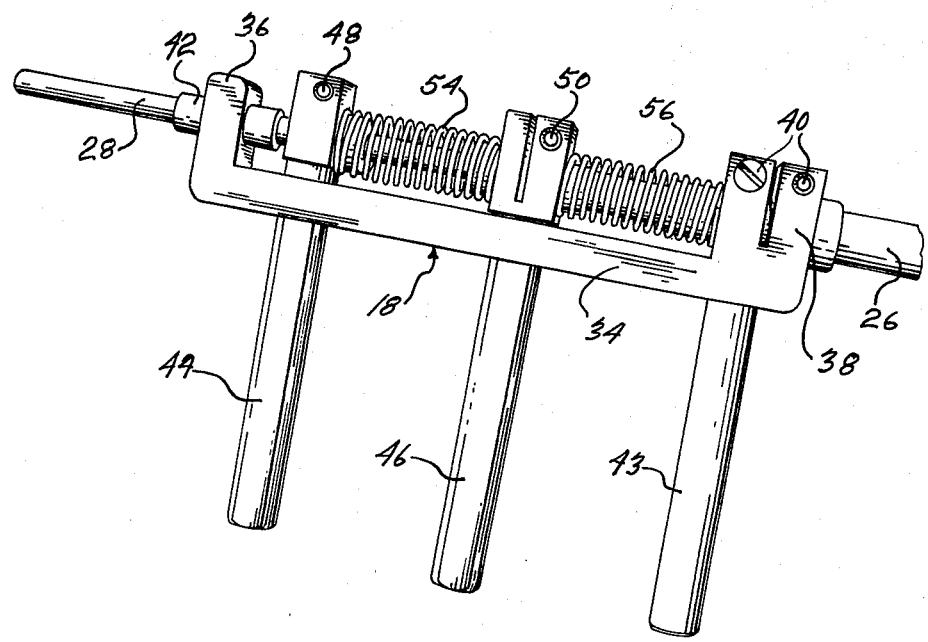
FIG. 5 illustrates an enlarged view of the handle assembly of FIGS. 1 and 2 for operating the end closures of the container of the sampler device.

Referring now to FIG. 5, there is shown the handle assembly 18 located at the other end of the holder. The handle assembly is U-shaped and consists of a long base portion 34 and two short legs 36 and 38. Leg 38 is secured to tube 26 by means of bolts 40 whereas a sleeve 42 is inserted into leg 36 for guiding tube 28 which, as mentioned previously, is secured to end closure 16. A supporting handle 43 is fixed to base portion 34 adjacent leg 38 whereas two operating handles 44 and 46 are secured to tube 28 and to holder 12 respectively by means of bolts 48 and 50. Handles 44 and 46 are movable in a slot 52 (FIGS. 1 and 2) in base portion 34 of the handle assembly and are biased into the position illustrated in FIGS. 1 and 5 by springs 54 and 56 located between handles 44 and 46 and between handle 46 and leg 38 so as to urge the end closures 14 and 16 against the ends of container 10.

To open the end closure 14, handle 46 is moved toward supporting handle 43. This moves the container 10 away from the end closure 14 and so open the container. It would be noted that during this movement the other end closure 16 follows but remains in contact with the container 10. Similarly, to open end closure 16, handle 44 is moved toward handle 46. Again it will be noted that during this movement, the end closure 14 remains in contact with the container. Therefore, end closures 14 or 16 may be operated separately. They may however be both open by moving handles 44 and 46 toward supporting handle 43. In the above embodiment end closure 14 acts as a reference and the holder 12 supporting container 10 and the other end closure 16 are movable. However, it will be understood that holder 12 or end closures 16 could act as a reference and the other elements be movable.

In use, the device of the invention with the end closures in the shut position in lowered in the body of slurry or liquid to be sampled, and either only the top end closure 14 or both end closures 14 and 16 are then opened to allow slurry or liquid to fill the sample container. The end closures are then shut, and the device withdrawn from the body of slurry or liquid. The sample is recovered by opening the bottom end closure 16 alone or the top and bottom end closures 14 and 16 together.

The main feature of the invention is that the sampler is sealed during immersion so that the inside of the container remains uncontaminated prior to taking the sample. The sampler is also sealed after taking the sample so as to avoid further contact with the body slurry or liquid after taking the sample.

One additional feature of the invention is the possibility, when collecting a sample of coarse slurry, of opening only the top end closure of the sample container. This ensures that the bottom closure remains water tight and that no sample leaks out during retrieval. If the bottom closure were opened while immersed in a coarse slurry, coarse particles of solid might deposit on the gasket and prevent tight sealing upon shutting the closure.

A further feature of the invention is that container 10 can be attached to holder 12 by means of a threaded connection and is therefore removable. Any volume of sample can be collected, between a few milliliters and several liters, by attaching a container 10 of suitable length. However, the invention is not limited to cylindrical sample containers although a cylindrical shape is most convenient.

Another important feature of the invention is the flexible joint 32 between the bottom closure 16 and the tube 28 which further ensures tight sealing of the end closures against the sample container.

In the above embodiment, the container 10 is positioned substantially vertically when immersed into the body of slurry or liquid and the end closures thus form top and bottom closures. However, it will be understood that the container 10 could be positioned at 90° with respect to its holder and thus be substantially horizontal when immersed into the body of slurry or liquid. The end closures would then have to be operated by adequate means adapted to such a design.

The above disclosed can be used to measure the pulp density of slurries faster and with greater accuracy than with existing pulp density scales, such as the well known Marcy scale. To obtain a measurement with the Marcy scale, a container is filled to an overflow level by pouring into it a slurry sample from a hand cutter. Generally, fractional amounts of the cutter contents must be added to top up the container to the overflow mark. This is difficult to do without avoiding settling of the slurry solids in the cutter. This shortcoming can be eliminated by using the device of FIGS. 1 to 5. The device can be hung from or placed on a suitable type of tared scale to give the weight, or by calibration, the percent solids of the volume of slurry in the sample container of the device, the solids content of the sample being accurately representative of that in the body of pulp from which the sample was taken.

Figure 6:
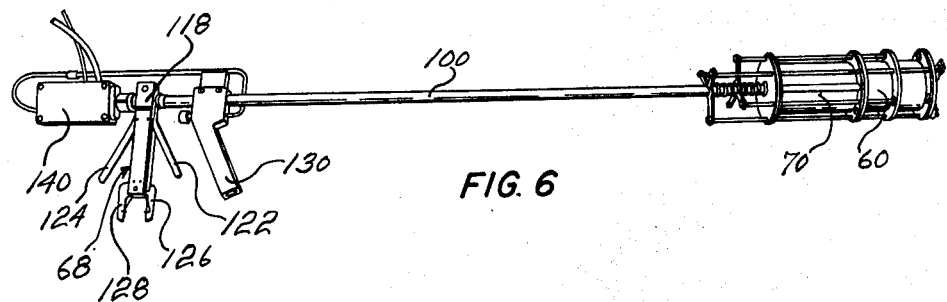
FIGS. 6 and 7 illustrate perspective views of a second embodiment of a sample device in accordance with the invention which is provided with an apparatus for measuring in situ the chemical or physical properties of a sample of slurry or liquid.
Figure 7:
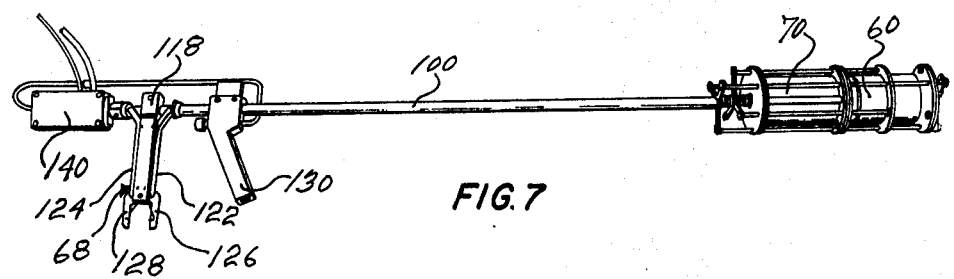

FIGS. 6 to 11 illustrate a second embodiment of the invention which is provided with means for measuring in situ desired chemical or physical properties of the sample. In such a device, the slurry or liquid in the container does not have to be transferred into a separate container or apparatus for measuring its properties. These can be measured while the sampler device is immersed in the body of slurry or liquid. As illustrated in FIGS. 6 and 7, this second embodiment of the invention comprises generally a container 60 secured to a holder 62 (FIG. 8) of suitable length for immersing the container into a body of slurry or liquid and provided with end closures 64 and 66 operated by a handle assembly 68. The end closure 64 forms part of a sealed housing 70 into which may be located any suitable apparatus extending into the container 60 for measuring desired chemical or physical properties of a sample in container 60 and a motor for operating a stirrer also extending into the container 60 as it will be disclosed later.

Figure 8:
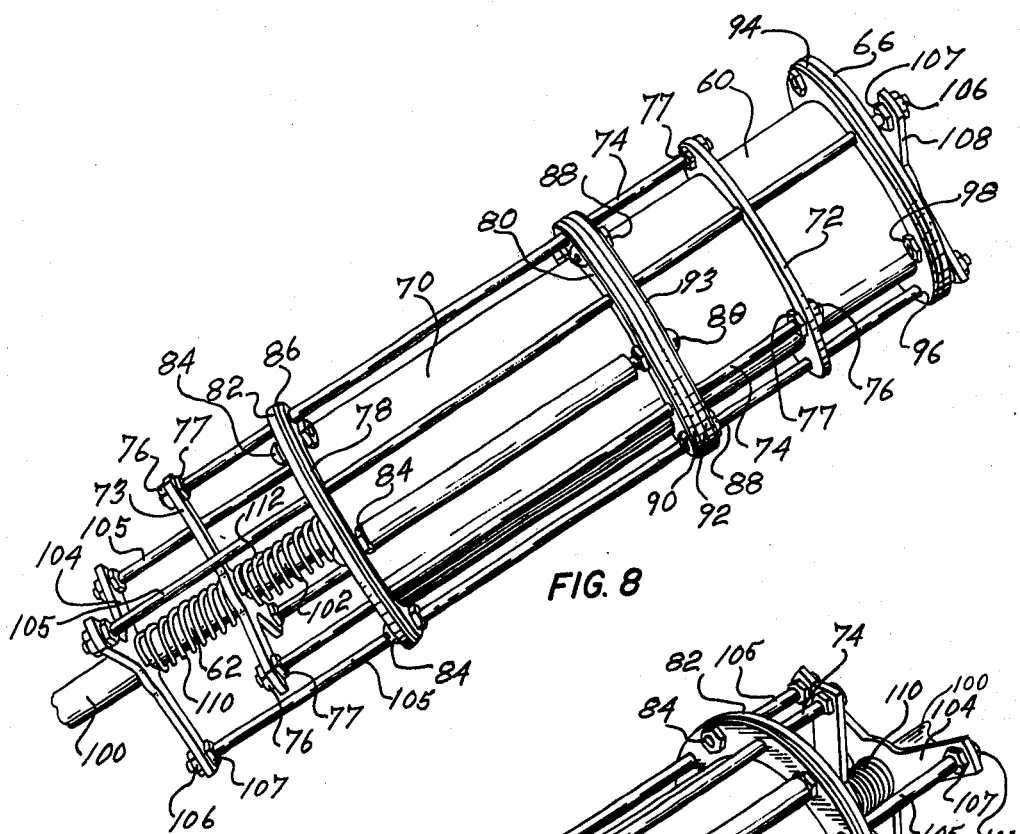
FIGS. 8 and 9 illustrate enlarged views of the device of FIGS. 1 and 2 in the closed and open positions respectively.
Figure 9:
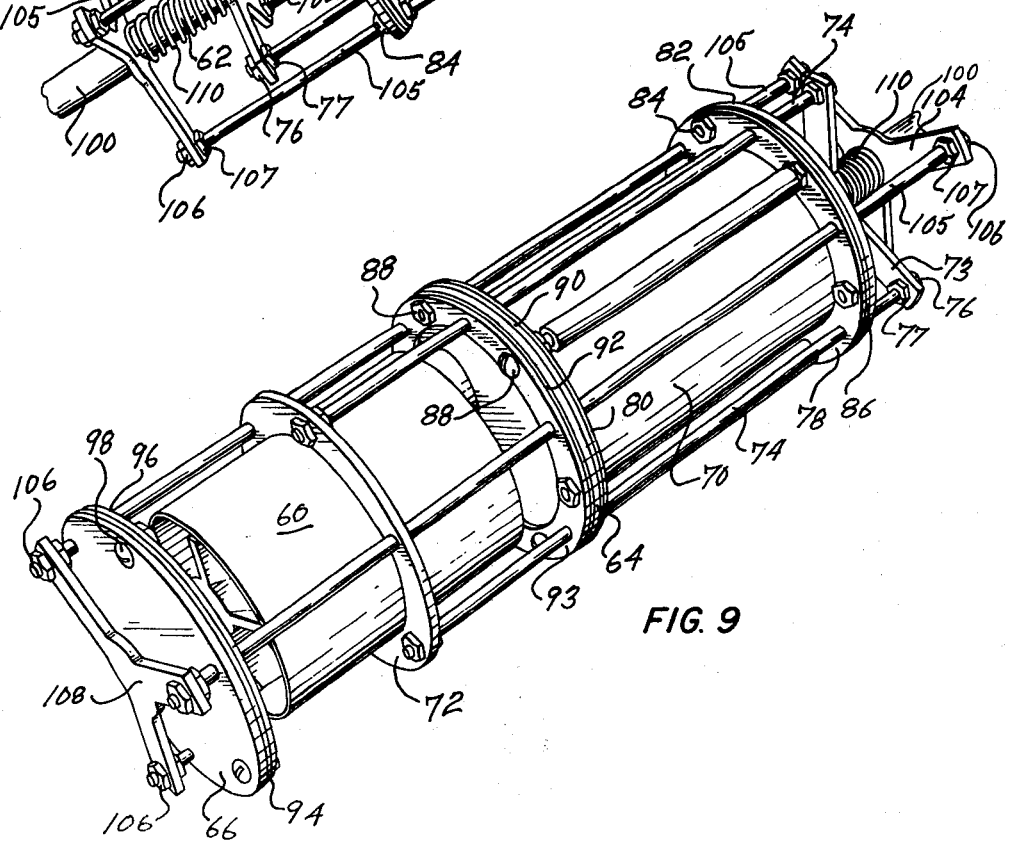
Figure 10:
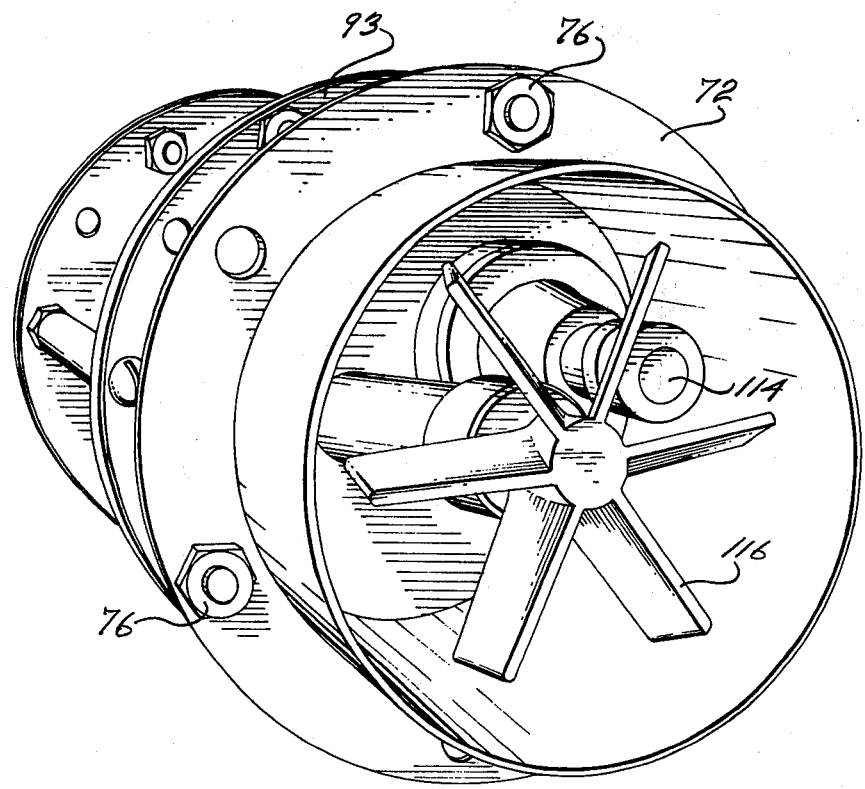
FIG. 10 illustrates an end view of the device of FIGS. 8 and 9 with the end closure removed showing the stirrer and the end of an oxygen probe protruding through the container.

Referring more particularly to FIGS. 8 to 10, container 60 is a cylinder provided with a central outside ring 72. The hub of a spider member 73 is secured to holder 62 and the container 10 is attached to holder 62 by means of rods 74 interconnecting the arms of spider member 73 and outside ring 72. The ends of the rods are secured to ring 72 and spider member 73 by means of tightening nuts 76 and lock nuts 77. The housing 70 is a cylinder provided with end flanges 78 and 80. One end of the cylinder is closed by plate 82 which is secured to flange 78 by bolts 84 and sealed by gasket 86 placed between plate 80 and flange 78. The other end of housing 70 is closed by the above mentioned end closure 64 which is secured to flange 80 by bolts 88 and sealed by gasket 90. Flanges 78 and 80 as well as plates 64 and 82 have holes therein through which rods 74 extend so as to maintain container 60 in alignment with housing 70. A further gasket 92 is placed on the side of end closure 64 opposite the housing 70 and such gasket is held in position by ring 93 and bolts 88. Gasket 92 seals one end of container 60 when closed against the bottom of the housing 70. Another gasket 94 is placed on the side of end closure 66 facing the container 60 and held in position by ring 96 and bolts 98. Gasket 94 seals the other end of container 60 when closed by end closure 66.

The means for opening and closing the end closures 64 and 66 may vary but, in the present embodiment, they consist of tubes 100 and 102 which are concentric with holder 62 and free to move longitudinally outside and inside holer 62 respectively. A spider member 104 having its hub portion secured to tube 100 and its arms secured to end closure 66 through rods 105 is used to move end closure 66 with respect to container 60. The ends of rods 106 are secured to their respective spider members by means of tightening nuts 106 and lock nuts 107. Rods 105 extend through holes in end closure 66 and are connected to a spider member 108 which is connected to end closure 66 through a central pivotal connection (not shown) similar to flexible ball joint 32 of FIG. 3. As mentioned previously in connection with the embodiment of FIG. 3, this permits tight sealing of the container 60. The end closure 66 is biased against container 60 by means of a spring 110 which is coaxially mounted with holder 62 between spider members 73 and 104. It will be noted that rods 105 extend through holes in end flanges 78 and 80, plates 64, 66 and 82 and rings 72 and 96 for maintaining proper alignment of end closure 66 with respect to container 60. In addition, the holes through end plate 66 and ring 96 are large enough to permit a small movement of the end closure as required by the flexible joint at the middle of spider member 108. Tube 102 is connected to housing 70 and the end closure 64 forming part of housing 70 is maintained in closed position against container 60 by means of spring 112 which is coaxial with tube 102 placed between spider member 73 and plate 82.

Referring now to FIG. 10, there is shown the end of an oxygen probe 114 for measuring the oxygen content of the sample. The oxygen probe 114 protrudes through the end closure 64 of housing 70 and gasket 92. As mentioned previously, the oxygen probe is located within housing 70 and is adapted to extend into container 60 for measuring the properties of the sample in the container 60. There is also shown a stirrer 116 the shaft of which extends through the end closure 64 and is connected to a motor (not shown) located in housing 70.

Figure 11:
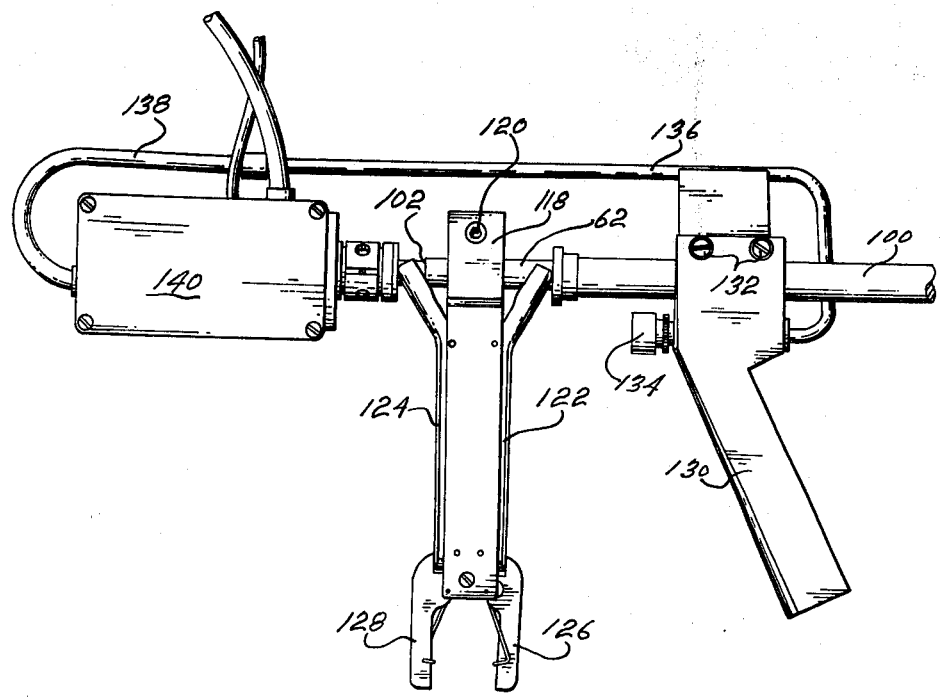
FIG. 11 illustrates an enlarged view of the handle assembly of FIGS. 6 and 7 in the operated position.

Referring now to FIG. 11, there is shown the handle assembly 68 including a reference handle 118 which is secured to holder 62 by bolt 120. Operating handles 122 and 124 are pivoted on reference handle 118 for operating tubes 100 and 102 respectively. As mentioned previously, the longitudinal movement of tubes 100 and 102 with respect to holder 62 opens container 60. Handles 122 and 124 may be locked in operated position by spring biased members 126 and 128 respectively so as to maintain container 60 in open position if desired while the sampler is immersed in the body of slurry or liquid. A control handle 130 may also be secured to tube 100 by bolts 132 and provided with a switch 134 for controlling the energization of the motor of the stirrer 116. The leads for the switch 134 are passed through a tube 136 having a flexible portion 138 and connected to a control box 140 secured to the end of tube 102. It will be understood that the leads going to housing 70 are passed through the center of tube 102.

It will be understood that the sampler device of FIGS. 6 to 11 shows only an example of an apparatus for measuring in situ desired chemical or physical properties of a sample of slurry or liquid and that various other embodiments are envisaged. For example, the means for opening and closing the movable end closures may vary as well as the form of handle assembly connected to the end closures. It will also be understood that any type of measuring apparatus such as oxygen probes, pH electrodes, etc., may be positioned in housing 70 depending on the properties to be measured.

The device of the invention, as described in FIGS. 6 to 11, has been used for measuring in situ the oxygen demand of ground ore slurries. After having filled the container 60 with the sample, the stirrer is operated to suspend the slurry and the rate of decrease of oxygen content is measured for a sufficient period of time, typically 1 to 5 minutes.

The device of the present invention is also suitable for sampling water or solutions containing little or no solids or in biological oxidation systems.

The device of the invention can be constructed of any material, metallic or plastic, compatible with the material to be sampled.

What is claimed is:

1. A device for taking samples of slurries or any suspension of particulate material in a liquid comprising:
    a. a container consisting of side walls and movable end closures;
    b. a holder of suitable length secured at one end to said container for immersing the container into a body of slurry or liquid; and
    c. means associated with said holder for tightly closing the end closures against the walls of the container and for opening at least one of said movable end closures, said means for closing and opening said end closures comprising separate connections associated with said holder and attached to each of said end closures, a handle assembly mounted at the other end of said holder and including separate handles for operating said connections, and spring means also mounted on said holder for biasing said connections with respect to each other in a direction such as to close the end closures.

2. A device as defined in claim 1, wherein said connections are mounted concentrically with said holder.

3. A device as defined in claim 2, wherein said holder is a straight tube and wherein said connections include a first tube free to move longitudinally inside the holder and attached at one end to one of the end closures and a secondd tube free to move longitudinally outside the holder and attached at one end of the other end closure.

4. A device as defined in claim 3, wherein each of said operating handles is fixed to the other end of a respective one of said tubes and the handle assembly further comprises an additional handle fixed to the other end of said holder, said spring means being mounted coaxially with said tubes and placed between said operating handles and said additional handle for biasing the operating handles away from said additional handle and so close the end closures.

5. A device as defined in claim 3, wherein the first tube is secured to its associated end closure by means of a flexible joint.

6. A device as defined in claim 1, wherein said holder is fixed to said container by means of a spider member having its arms secured to the walls of the container and its hub secured to said one end of the holder.

7. A device as defined in claim 6, wherein said side walls are in the form of a cylinder and further comprising a ring secured to the end of the arms of the spider member, said cylinder being threaded onto said ring so as to permit attachment of cylinders of various lengths to suit different volumes of sample.

8. A device as defined in claim 7, further comprising a gasket secured to the periphery of the end closures and adapted to contact the side walls of the container at one end thereof and the ring at the other end thereof for sealing the container when closed.

9. A device as defined in claim 1, further comprising a gasket secured to the periphery of the end closures and adapted to contact the side walls of the container for sealing the same when closed.

10. A device as defined in claim 1, futher comprising means associated with one of said end closures for measuring in situ desired chemical or physical properties of said sample.

11. A device as defined in claim 10, wherein said means includes a sealed housing enclosing a motor having a shaft protruding through said one closure for operating a stirrer located in said container, and suitable apparatus also protruding through said one end closure and adapted to contact the sample contained in said container for measuring the properties thereof.

12. A device as defined in claim 11, wherein said holder is a straight tube which is secured to said container through a first spider member having its hub secured to the straight tube and its arms secured to the walls of the container through rods extending from said arms to said walls, and wherein said connections include a first tube free to move longitudinally inside the holder and attached to one end of said housing, and a second tube free to move longitudinally outside the holder and which is secured to the other end closure through a second spider member having its hub secured to the second tube and its arms secured to said other end closure through rods extending from said arms to said other end closure.

13. A device as defined in claim 12, wherein said housing and said container are provided with outer flanges or rings through which the rods extending from said first and second spider members pass so as to ensure alignment of the container and of said other end closure.

14. A device as defined in claim 12, wherein said spring means are mounted coaxially with said tubes and placed between said first and second spider members and between said housing and said first spider respectively so as to bias said other end closure against said container and said container against said housing to hermetically close said container.

15. A device as defined in claim 12, wherein said second spider member is secured to said other end closure through a flexible joint.

16. A device defined in claim 15, wherein said flexible joint includes a third spider member having its hub pivotally mounted to said other end closure and its arms connected to the rods joined to the arms of the second spider member.

17. A device as defined in claim 12, further comprising a reference handle secured to the other end of said holder and wherein the handles operating the first and second tubes are pivotally mounted on said reference handle.

18. A device as defined in claim 17, further comprising means for locking the handles operating the first and second tubes in operated position for maintaining the container open when immersing the container into the body of slurry or liquid.

19. A device as defined in claim 12, further comprising a control handle mounted on the other end of said second tube, said control handle being provided with a manual switch for energizing said motor.

20. A device as defined in claim 12, further comprising a control box for said motor and said apparatus mounted on the other end of said first tube.

* * * * *